(12) United States Patent
Wang

(10) Patent No.: US 6,207,398 B1
(45) Date of Patent: Mar. 27, 2001

(54) CYCLOSPORINE DERIVATIVES AND USES THEREOF

(75) Inventor: Chengrong Wang, Hockessin, DE (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 09/372,285

(22) Filed: Aug. 11, 1999

Related U.S. Application Data

(62) Division of application No. 08/978,051, filed on Nov. 25, 1997, now Pat. No. 5,990,274.

(51) Int. Cl.[7] ............... G01N 33/553; G01N 33/552; G01N 33/548; C07K 16/44
(52) U.S. Cl. .............. 435/7.93; 436/526; 436/527; 436/529; 436/530; 436/531; 530/389.8; 530/404; 530/405
(58) Field of Search ............ 435/7.93; 530/389.8, 530/404, 405; 436/526, 530, 529, 531, 527

(56) References Cited

U.S. PATENT DOCUMENTS

| | | |
|---|---|---|
| 4,117,118 | 9/1978 | Hårri et al. . |
| 4,384,996 | 5/1983 | Bollinger et al. . |
| 4,396,542 | 8/1983 | Wenger . |
| 4,639,434 | 1/1987 | Wenger et al. . |
| 4,661,408 | 4/1987 | Lau et al. . |
| 4,727,035 | 2/1988 | Mahoney . |
| 4,764,503 | 8/1988 | Wenger . |
| 4,798,823 | 1/1989 | Witzel . |
| 5,089,390 | 2/1992 | Davalian et al. . |
| 5,151,348 | 9/1992 | Lau et al. . |
| 5,169,773 | 12/1992 | Rosenthaler et al. . |
| 5,239,057 | 8/1993 | Wang et al. . |
| 5,302,532 | 4/1994 | Lau . |
| 5,350,574 | 9/1994 | Erlanger et al. . |
| 5,405,785 | 4/1995 | Erlanger et al. . |
| 5,489,668 | * 2/1996 | Morrison et al. ............ 530/321 |

FOREIGN PATENT DOCUMENTS

| | | |
|---|---|---|
| 0 044 441 A1 | 1/1982 | (EP) . |
| 0 283 801 A2 | 9/1988 | (EP) . |
| 0 375 454 A1 | 6/1990 | (EP) . |
| 0 473 961 A2 | 3/1992 | (EP) . |
| 0 487 289 A2 | 5/1992 | (EP) . |
| 0 487 289 B1 | 5/1992 | (EP) . |
| WO 86/02080 | 4/1986 | (WO) . |
| WO 90/06763 | 6/1990 | (WO) . |

OTHER PUBLICATIONS

*Pagageorgiou, et al., Bioorganic & Medicinal Chemistry Letters, 3 No. 12:2559–2564,1993.

*Rauffer, et al., Molecular Immunology, 31 No 12:913–922, 1994.

*Ball, et al.; *Specific [3]H Radioimmunoassay with a Monoclonal Antibody for Monitoring Cyclosporine in Blood*, Clinical Chemistry; 34 No. 2:257–260, 1988.

*Bowers, et al.; *Studies of Cyclosporine Blood Levels: Analysis, Clinical Utility, Pharmacokinetics, Metabolites, and Chronopharmacology*; Transplantation Proceedings; XVIII No. 6, Suppl 5:137–143, 1986.

* Cacalano, et al.; *Antibodies to cyclosporine A (CsA) by a novel route and their use to monitor cyclosporine levels by radioimmunoassay*; J. Immunological Methods; 118:257–263, 1989.

*Christians, et al.; *Liquid–Chromatographic Measurement of Cyclosporin A and Its Metabolites in Blood, Bile, and Urine*; Clinical Chemistry; 34 No. 1:34–39, 1988.

*Donatsch, et al.; *A radioimmunoassay to measure cyclosporin A in plasma and serum samples*; J. Immunoassay; 2 No. 1:19–32, 1981.

*Hawk's Cay Meeting; *Consensus Document: Hawk's Cay Meeting on Therapeutic Drug Monitoring of Cyclosporine*; Transplantation Proceedings; 22 No. 3:1357–1361, 1990.

*Mauer, et al.; *Disposition of cyclosporine in several animal species and man*; Drug Metabolism And Disposition; 12 No. 1:120–126, 1984.

*McBride, et al.; *Measurement of Cyclosporine in Plasma from Patients with Various Transplants: HPLC and Radioimmunoassay with a Specific Monoclonal Antibody Compared*; Clinical Chemistry; 35 No. 8:1726–1730, 1989.

*Quesniau, et al.; *An enzyme immunoassay for the screening of monoclonal antibodies to cyclosporin*; Immunology Letters; 9:99–104, 1985.

*Quesniaux, et al.; *Fine specificity and cross–reactivity of monoclonal antibodies to cyclosporine*; Molecular Immunology; 24 No. 11:1159–1168, 1987.

*Quesniau, et al.; *Potential of Monoclonal Antibodies to Improve Therapeutic Monitoring of Cyclosporine*; Clinical Chemistry; 33 No. 1:32–37, 1987.

* Quesniaux, et al.; *Monoclonal Antibodies to Ciclosporin*; Prog. Allergy; 38:108–122,1986.

* Rosano, et al.; *Cyclosporine Metabolites in Human Blood and Renal Tissue*; Transplantation Proceedings; XVIII No. 6 Supp. 5:35–40, 1986.

*Ryffel, et al.; *Biologic Significance of Cyclosporine Metabolites*; Transplantation Proceedings; XX No. 2 Supp. 2:575–584, 1988.

*Sandoz Ltd.; Ciclosporin RIA–Kit, Instructions for Use; 2nd Edition:1–21, 1983.

(List continued on next page.)

Primary Examiner—Mary E. Ceperley
(74) Attorney, Agent, or Firm—Patrick G Gattari

(57) ABSTRACT

The present invention provides novel cyclosporine C (CsC) derivatives having improved protein conjugatibility and hydrolytic stability. The present invention further provides a CsC derivative conjugated to a carrier, e.g., a solid support. Preferably, the solid support is a latex or magnetic particle.

11 Claims, No Drawings

OTHER PUBLICATIONS

* Sanghvi, et al.; *Abbott's Fluorescence Polarization Immunoassay for Cyclosporine and Metabolites Compared with the Sandoz "Sandimmune" RIA*; Clinical Chemistry; 34 No. 9:1904–1906, 1988.

*Traber, et al.; *Cyclosporins—New Analogues by Precursor Directed Biosynthesis*; Journal of Antibiotics; XLII No. 4:591–597, 1988.

*Schran, et al.; *Determination of Cyclosporine Concentrations with Monoclonal Antibodies*; Clinical Chemistry; 33 No. 12:2225–2229, 1987.

*Vermillet, et al.; *Determination of Cyclosporine in Plasma: Specific Radioimmunoassay with a Monoclonal Antibody and Liquid Chromatography Compared*; Clinical Chemistry; 35 No. 4:608–611, 1989.

*Wolf, et al.; *Measurement of Cyclosporine Concentrations in Whole Blood: HPLC and Radioimmunoassay with a Specific Monoclonal Antibody and $^{3}H$–or $^{125}I$–Labeled Ligand Compared*; Clinical Chemistry; 35 No. 1:120–124, 1989.

*Erlanger, Bernard F.; *The Preparation of Antigenic Hapten–Carrier Conjugates: A Survey*; Methods in Enzymology; 70:85–105, 1980.

*Kabakoff, David S.; *Chemical Aspects of Enzyme–Immunoassay*; ISRN 0–8493–5617–2; Chap. 4:71–104, 1987.

*Brinkley, Michael; *A Brief Survey of Methods for Preparing Protein Conjugates with Dyes, Haptens, and Cross–Linking Reagents; Teaching Editorial*; Bioconjugate Chem; 3 No. 1:2–13, 1992.

*Yatscoff, et al.; *Pharmacodynamic Monitoring of Immunosuppressive Drugs*; Transplantation Proceedings; 28 no. 6:3013–3015, 1996.

* cited by examiner

CYCLOSPORINE DERIVATIVES AND USES THEREOF

This application is a divisional of U.S. patent application Ser. No. 08/978,051 filed Nov. 25, 1997, U.S. Pat. No. 5,990,274.

BACKGROUND OF THE INVENTION

1. Field of the Invention

The present invention relates to novel cyclosporine derivatives that have improved protein and solid surface conjugatibility and hydrolytic stability. The cyclosporine derivatives of the present invention are useful in assays measurement of cyclosporin A levels, as well as in the production of cyclosporine immunogens and capture conjugates.

2. Background

Cyclosporine A (cyclosporine) is a potent immunosuppressant that has been widely used in the United States and other countries to prevent the rejection of transplanted organs such as kidney, heart, bone marrow and liver, in humans.

To prevent allograft rejections, minimum level cyclosporine A in the blood is required throughout the lifetime of the patient. Chronic high doses can result in kidney and liver damage. Distribution and metabolism of the drug varies greatly between individuals, as well as in a single individual during the course of therapy. Accordingly, monitoring cyclosporine A levels in the blood or serum of allograph recipients is considered essential.

Laboratory methods for detection of cyclosporine have been developed. These techniques typically involve high performance liquid chromatography (HPLC), radioimmunoassay (RIA) and non-radioimmunoassay.

It has been reported that CsA, itself, is non-immunogenic (Donatsch, p. et al., J. Immuno Assay 1981; 2:19). To obtain antibodies, therefore, it is necessary to link CsA to a protein carrier. The side chain of CsA, however, consists most of alliphatic groups. Few of the functional groups customarily used to link a hapten to a carrier. Previous workers have made immunogenic cyclosporine C (CsC) protein conjugates because the CsC has a threonine residue in position 2. Linkage to a protein was via a hemisuccinate linker through an ester group (U.S. Pat. No. 5,169,773). In addition, hemisuccinate coupling chemistry has been used to immobilize CsC to a solid support such as stabilized chromium dioxide particles (U.S. Pat. No. 5,151,348). Due to a number of factors including, for example, short chain length of the hemisuccinate linker, hydrophobicity of the cyclosporine-C hemisuccinate molecule and hydrolytic instability of the hemisuccinate ester linkage, the CsC hemisuccinate derivatives conjugate poorly to protein and solid surface. Furthermore, CsC protein conjugates and CsC immobilized on a solid support by hemisuccinate coupling, are hydrolyticly unstable. Thus, immunoassays developed by using such hemisuccinate CsC derivatives suffer from low sensitivity and poor reagent stability. There is a strong desire to replace the widely used radioimmunoassays and HPLC methods with a more robust and sensitive immunoassay for CsA. Accordingly, there is a need in the art for cyclosporine derivatives that are capable of being conjugated to solid supports and carriers more efficiently and stably.

SUMMARY OF THE INVENTION

The present invention provides novel cyclosporine C (CsC) derivatives having improved protein conjugatibility and hydrolytic stability. The present invention further provides a CsC derivative conjugated to a carrier, e.g., a solid support. Preferably, the solid support is a latex or magnetic particle.

The invention also provides improvements in assays for the determination of cyclosporin levels in a sample, e.g., whole blood, suspected of containing cyclosporin.

Furthermore, the invention includes kits for conducting an assay for the determination of cyclosporin. The present invention also provides for the production of cyclosporine immunogens and capture conjugates comprising the CsC derivatives of the present invention.

DETAILED DESCRIPTION OF THE INVENTION

The present invention relates to cyclosporine C (CsC) derivatives having the structure:

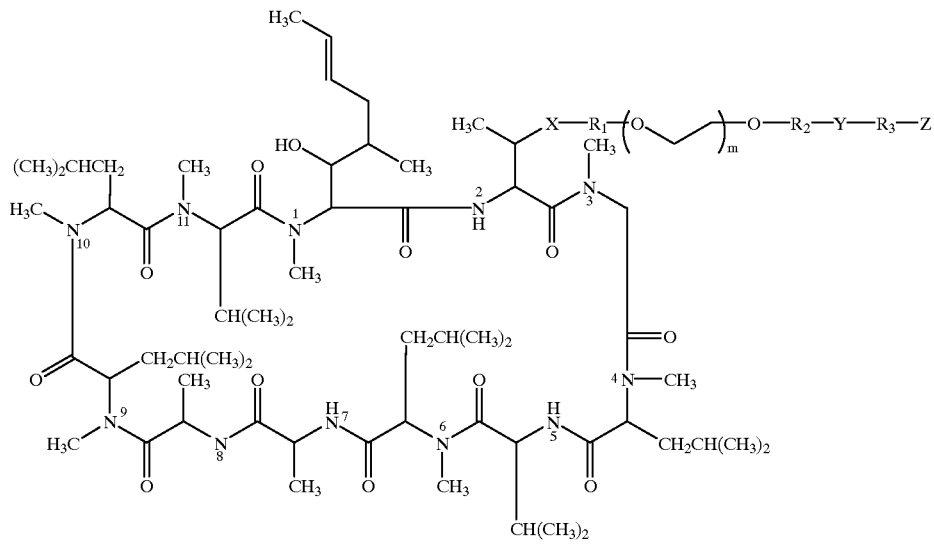

X is selected from the group consisting of:

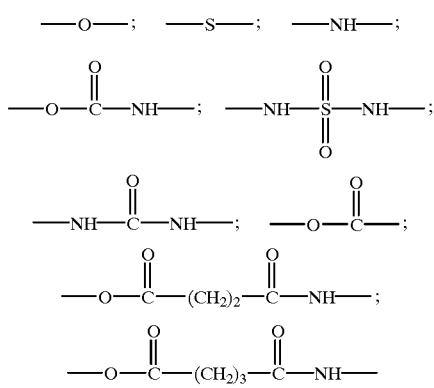

Y is selected from the group consisting of:

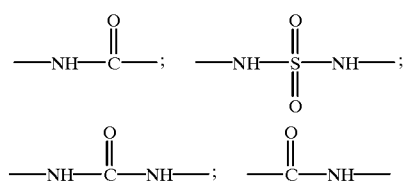

-continued

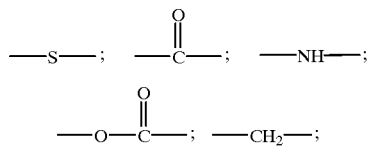

wherein Z is selected from the group consisting of:

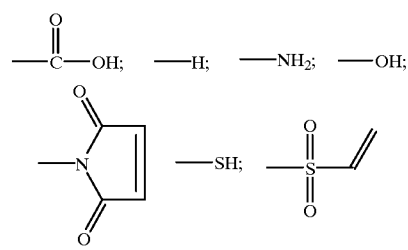

wherein $R_1$ and $R_2$ are each a C1–C8 alkyl group;
wherein $R_3$ is a $C_0$–$C_8$ alkyl group; and
wherein m is 1–200

A particular embodiment of the present invention includes CsC derivatives having the following structures:

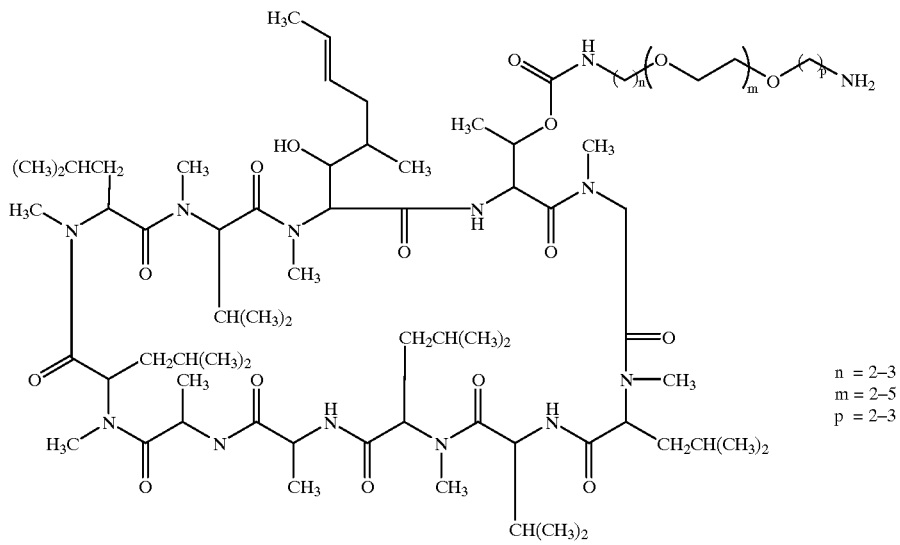

n = 2–3
m = 2–5
p = 2–3 and

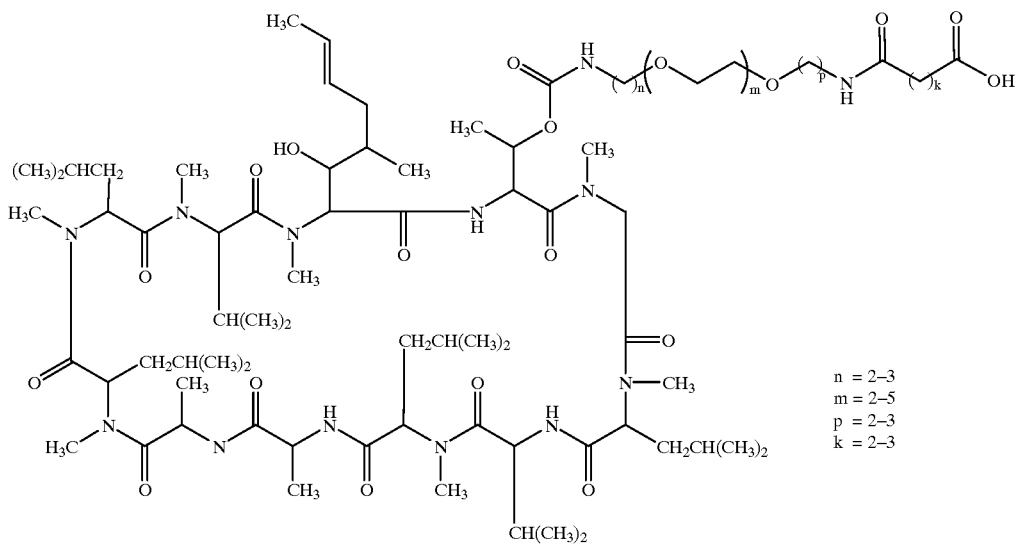

n = 2–3
m = 2–5
p = 2–3
k = 2–3

The CsC derivatives of the present invention were prepared by activation of the CsC position 2 hydroxy group using disuccinimidyl carbonate followed by coupling with linkers such as diamine linkers, e.g., ethylene glycol bis(2-aminoethyl)ether (DA-10). The following scheme illustrates the application of this procedure to the synthesis of the CsC derivatives of this invention:

Starting materials used in the above-described scheme are either known or commercially available.

The CsC derivatives of the present invention may be used in immunoassay for the measurement of cyclosporin A levels in whole blood samples. An example of such an assay comprises the steps of:

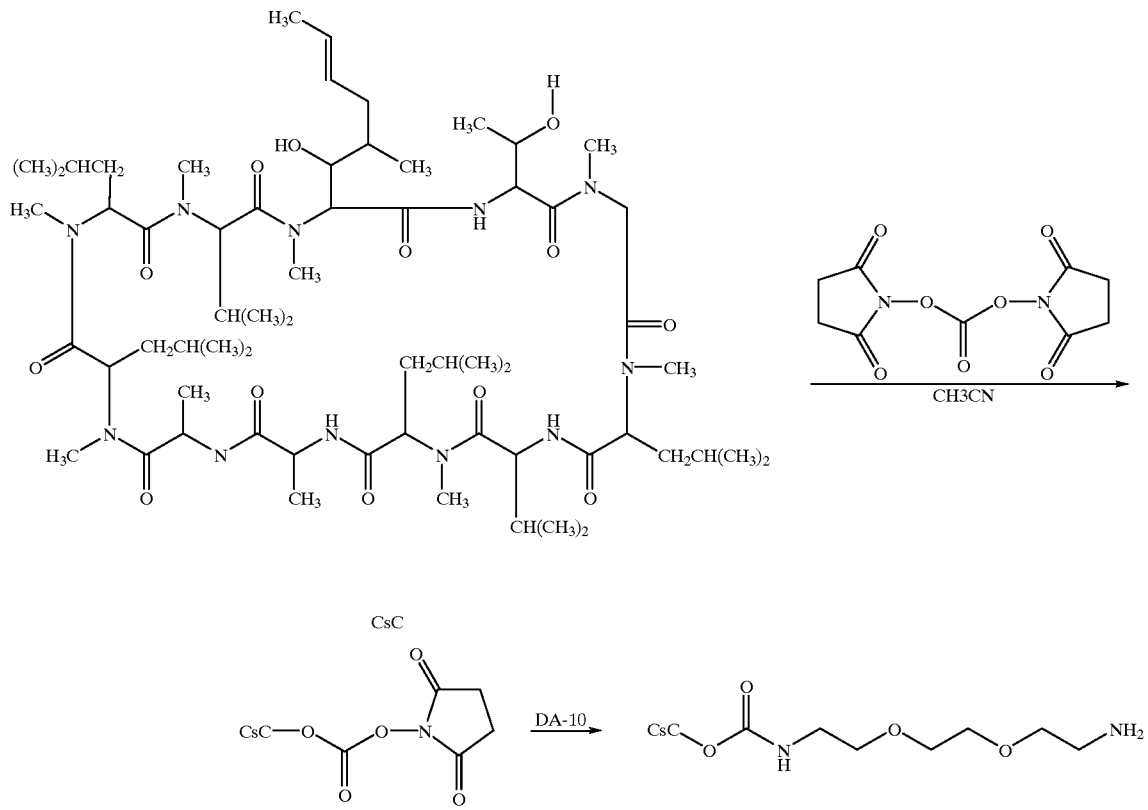

(a) lysing red blood cells in a sample of whole blood containing cyclosporin A;

(b) contacting the lysed whole blood sample with excess labeled anti-cyclosporin antibody, e.g., beta-D-galactosidase labeled, to form a labeled antibody-cyclosporin A complex;

(c) separating unbound antibody from the complex by contacting the mixture formed in step (b) with a solid phase comprising a cyclosporin derivative of the present invention immobilized on a solid support; and (d) determining the amount of the label in the complex as a measure of cyclosporin A, using, for example, a beta-D-galactosidase substrate selected from the group consisting of chlorophenol red-beta-D-galactopyranoside (CPRG) and resorufin-beta-D-galactopyranoside (ReG) if a beta-D-galactosidase label is used.

The enzyme-linked immunoassay of this invention is useful for measuring cyclosporin A levels in whole blood samples of patients receiving cyclosporin A. Monitoring of cyclosporin A blood levels and subsequent cyclosporin A dosage adjustment are necessary to prevent toxic effects caused by high cyclosporin A blood levels and to prevent organ rejection caused by low cyclosporin A blood levels.

The immunoassay of the present invention is performed by contacting a lysed whole blood sample containing cyclosporin A with excess labeled anti-cyclosporin antibody, e.g., beta-D-galactosidase-labeled, to form a reaction mixture containing a complex of cyclosporin A with labeled antibody and free labeled antibody, separating free antibody from the reaction mixture by contacting the reaction mixture with a solid phase comprising an immobilized CsC derivative of the present invention on a solid support, e.g. magnetic particles, separating the solid phase from the liquid phase, and measuring the amount of the bound label in the liquid phase by adding, for example, to the liquid phase CPRG or ReG as a beta-D-galactosidase substrate if a beta-D-galactosidase label is used.

Specifically, the red blood cells of a whole blood sample containing cyclosporin A must be lysed to release cyclosporin A. Red blood cell lysis can be accomplished by many methods, such as sonication, detergent lysis and distilled water lysis. The lytic agent chosen should be compatible with the labeled anti-cyclosporin antibody. Although some detergents can denature-beta-D-galactosidase, it has been found that by using CPRG and ReG as beta-D-galactosidase substrates, the sample volume can be made to be sufficiently small to minimize the denaturing effect of the detergent. The preferred lysis method uses detergent.

After lysis, a reaction mixture is formed by contacting the lysed whole blood sample with excess labeled anti-cyclosporin antibody and incubating the reaction mixture for a time and at a temperature sufficient to permit the labeled antibody to form a complex with all of the cyclosporin A in the sample. This usually takes 1–5 minutes at room temperature. Anti-cyclosporin antibody can be obtained commercially, prepared by known methods, or prepared using the derivatives of the present invention. The anti-cyclosporin antibody can be polyclonal or monoclonal. A monoclonal anti-cyclosporin antibody specific for cyclosporin A is preferred. The anti-cyclosporin antibody can be labeled using standard techniques with any molecule that can be detected, including, for example, radioactive isotopes, a catalyst such as an enzyme (e.g., beta-D-galactosidase), a co-enzyme, a chromogen such as a fluorescer, dye or chemiluminescer, a dispersible particle that can be non-magnetic or magnetic, a solid support, a liposome, a ligand, a hapten, and so forth.

The unbound anti-cyclosporin antibody is separated from the reaction mixture by contacting the reaction mixture with a solid phase comprising a CsC derivative of the present invention immobilized on a solid support for a time sufficient to permit the unbound labeled antibody to form a complex with the immobilized CsC derivative. This usually occurs in approximately one minute.

The immobilization of the CsC derivative of the present invention can be accomplished by a number of known immobilization techniques. The preferred immobilization technique for derivatives of the present invention is to activate the terminal carboxy group, using for example, 2-Fluoro-1methylpyridiniu-m p-toluenesulfonate (FMPT), and then coupling to a protein, such as albumin or globulin, which can be covalently coupled to a solid support.

The CsC derivative can be immobilized on a variety of solid supports such as beaded dextran, beaded agarose, polyacrylamide, or glass. A preferred solid support useful in the immunoassay of this invention is described in U.S. Pat. No. 5,151,348 and 5,302,532.

The preferred solid support comprises a stabilized chromium dioxide particles having cyclosporin bound to their surfaces. The stabilized chromium dioxide particle useful in the preferred solid support are those described in U.S. Pat. No. 4,661,408. These particles consist of a core of rutile chromium dioxide which has been extensively surface reduced, coated with alumina, further coated with silica containing borate and still further coated with a silane to which is attached cyclosporin protein conjugate, such as bovine gamma globulin. These particles have large surface areas, 40–100 $m^2/g$, are stable in aqueous solution and can be readily coupled to cyclosporin conjugate.

The support can also be a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass, ceramics, metals, and the like.

The solid phase is separated from the liquid phase by standard separation techniques. The preferred separation technique is to use magnet to settle the magentic particle out of liquid phase.

The amount of cyclosporin A is determined by measuring the amount of the bound label in the liquid phase. For example, the amount of bound beta-D-galactosidase is determined by adding to the liquid phase either CPRG or ReG as a beta-D-galactosidase substrate and measuring spectrophotometrically the amount of chromophore produced at 577 nm.

The immunoassay of this invention can be performed manually or it can be adapted to a variety of automated or semi-automated instrumentation, such as the Dimension® RxL (discrete clinical analyzer, a registered trademark of Dade International Inc. Deerfield, Ill.). In performing the assay on a Dimension® RxL, a whole blood sample is first lysed and preincubated with excess beta-D-galactosidaselabeled anti-cyclosporin antibody in a cuvette on the instrument. A known amount of stabilized chromium dioxide particle immobilized with CsC derivative of present invention is transferred into the cuvette and incubated for certain amount time, use magnet to separate the magnetic particle from liquid phase. The liquid phase of supernatant contains beta-D-galactosidase-labeled anti-cyclosporin antibody complexed with cyclosporin A from the whole blood sample. A fraction of the supernatant is pipetted and transferred to another cuvette with the addition of CPRG or ReG immediately preceding the absorbance measurements at 577 nm.

The present invention further provides a CsC derivative conjugated to a carrier, which is generally a compound of molecular weight greater than 5,000, or a label. Carriers include polyamino acids, lipopolysaccharides, and particles. The CsC conjugate can be used in many applications including as a capture conjugate in an assay or as an immunogen. The carrier may be immunogenic, i.e,. an immunogenic carrier.

The poly(amino acids) will generally range from about 5,000 molecular weight, having no upper molecular weight limit, normally being less than 10,000,000, usually not more than about 600,000 daltons.

Various protein types may be employed as the poly(amino acid) immunogenic material. These types include albumins, serum proteins, e.g., globulins, ocular lens proteins, lipoproteins, etc. Illustrative proteins include bovine serum albumin, keyhole limpet hemocyanin, egg ovalbumin, bovine gamma-globulin, etc. Alternatively, synthetic poly (amino acids) may be utilized.

The immunogenic carrier can also be a polysaccharide, which is a high molecular weight polymer built up by repeated condensations of monosaccharides. Examples of polysaccharides are starches, glycogen, cellulose, carbohydrate gums, such as gum arabic, agar, and so forth. The polysaccharide can also contain polyamino acid residues and/or lipid residues.

The immunogenic carrier can also be a nucleic acid either alone or conjugated to one of the above mentioned poly (amino acids) or polysaccharides.

The carrier can also be a particle. The particles are generally at least about 0.02 microns and not more than about 100 microns, usually at least about 0.05 microns and less than about 20 microns, preferably from about 0.3 to 10 microns diameter. The particle may be organic or inorganic, swellable or non-swellable, porous or non-porous, preferably of a density approximating water, generally from about 0.7 to about 1.5 g/ml, and composed of material that can be transparent, partially transparent, or opaque. The particles can be biologic materials such as cells and microorganisms, e.g., erythrocytes, leukocytes, lymphocytes, hybridomas, streptococcus, staphylococcus aureus, *E. coli*, viruses, and the like. The particles can also be particles comprised of organic and inorganic polymers, liposomes, latex particles, phospholipid vesicles, chylomicrons, lipoproteins, chrome and the like.

The particles can be derived from naturally occurring materials, naturally occurring materials which are synthetically modified and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

The particles will usually be polyfunctional and will be bound to or be capable of binding to the CsC derivative. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cautrecasas, J. Biol. Chem. (1970) 245:3059.

The carrier can be an enzyme that is part of a signal producing system. The function of the signal producing system is to produce a product which provides a detectable signal related to the amount of bound and unbound label. Where enzymes are employed, the involved reactions will be, for the most part, hydrolysis or redox reactions. Such enzymes that may find use are hydrolases, transferases, lyases, isomerases, ligases or synthetases and oxidoreductases, preferably hydrolases. Alternatively, luciferases may be used such as firefly luciferase and bacterial luciferase.

A label may be any molecule conjugated to an analyte or an antibody, or to another molecule. In the subject invention, the label can be a member of the signal producing system that includes a signal producing means. The label may be isotopic or nonisotopic, preferably nonisotopic. By way of example and not limitation, the label can be a catalyst such as an enzyme, a co-enzyme, a chromogen such as a fluorescer, dye or cherniluminescer, a dispersible particle that can be non-magnetic or magnetic, a solid support, a liposome, a ligand, a hapten, and so forth.

The signal producing system may have one or more components, at least one component being a label. The signal producing system includes all of the reagents required to produce a measurable signal including signal producing means capable of interacting with the label to produce a signal.

The signal producing system provides a signal detectable by external means, normally by measurement of electromagnetic radiation, desirably by visual examination. For the most part, the signal producing system includes a chromophoric substrate and enzyme, where chromophoric substrates are enzymatically converted to dyes which absorb light in the ultraviolet or visible region, phosphors or fluorescers.

The signal producing means is capable of interacting with the label to produce a detectable signal. Such means include, for example, electromagnetic radiation, heat, chemical reagents, and the like. Where chemical reagents are employed, some of the chemical reagents can be included as part of a developer solution. The chemical reagents can include substrates, coenzyrnes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to other molecules or to a support.

The signal producing system including the label can include one or more particles, which are insoluble particles of at least about 50 nm and not more than about 50 microns, usually at least about 100 nm and less than about 25 microns, preferably from about 0.2 to 5 microns, diameter. The particle may be organic or inorganic, porous or non-porous, preferably of a density approximating water, generally from about 0.7 to about 1.5 g/ml, and composed of material that can be transparent, partially transparent, or opaque.

The label can also be fluorescent either directly or by virtue of fluorescent compounds or fluorescers bound to a particle in conventional ways.

The fluorescers will usually be capable of, or functionalized to render them capable of, being bound to the CsC derivative or to the particle.

The CsC derivatives of the present invention can be utilized to prepare conjugates using the reactions discussed above and set forth in the examples.

Another aspect of the present invention includes antibodies prepared in response to a CsC derivative conjugated to an immunogenic carrier. Furthermore, the present invention includes conjugates of such antibodies and a label.

An antibody is an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera from which the immunoglobulin can be separated by known techniques (polyclonal) or by preparing continuous hybrid cell lines and collecting the secreted protein (monoclonal). Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like.

Monoclonal antibodies can be obtained by the process discussed by Milstein and Kohler and reported in Nature, 256:495–497, 1975.

The antibodies of the present invention recognize the cyclosporins including cyclosporin A and derivatives and metabolites of cyclosporins.

The antibodies of the present invention can be utilized in the determination of cyclosporin in a sample suspected of containing cyclosporin. The assay can comprise the steps of contacting the sample with antibodies for cyclosporin and detecting either directly or indirectly immune complexes of the antibodies and cyclosporin. The improvement provided in the present invention is the utilization of the present antibodies as the antibodies for cyclosporin. The immune complexes are detected directly, for example, where the antibodies employed are conjugated to a label. The immune complex is detected indirectly by examining for the effect of immune complex formation in an assay medium, on a signal producing system or by employing a labeled antibody that specifically binds to an antibody of the invention.

In another configuration of an assay for the determination of cyclosporin in a sample suspected of containing cyclosporin, the sample is contacted with antibodies for cyclosporin and a conjugate of this invention recognized by the antibodies. The method further includes detecting either directly or indirectly immune complexes of the conjugate and the antibodies. The improvement provided in the present invention is employing as the CsC derivative conjugated to a label.

The present assay invention has application to all immunoassays for cyclosporin. The assay can be performed either without separation (homogeneous) or with separation (heterogeneous) of any of the assay components or products. Exemplary of heterogeneous assays are enzyme linked immunoassays such as the enzyme linked immunosorbant assay (ELISA), see "Enzyme-Immunoassay" by Edward T. Maggio, CRC Press Incorporated, Boca Raton, Fla., 1980. Homogeneous immunoassays are exemplified by enzyme multiplied immunoassay techniques (e.g. see U.S. Pat. No. 3,817,837), immunofluorescence methods such as those disclosed in U.S. Pat. No. 3,993,345, enzyme channeling techniques such as those disclosed in U.S. Pat. No. 4,233,402, and other enzyme immunoassays as discussed in Maggio, supra.

The references cited throughout the specification are herein incorporated by reference.

The present invention is further illustrated by the following Examples. These Examples are provided to aid in the understanding of the invention and are not construed as a limitation thereof.

EXAMPLE 1

Synthesis of CsA-DA-10

In a 25 mL round bottom flask equipped with magnetic stirrer, 540 mg of CsC and 454 mg of DSC (disuccinimidyl carbonate) was placed, then 10 mL of dry acetonitrile and 1000 $\mu$L of triethyl amine were added. The reaction was stirred at room temperature for about 16–20 hours until no CsC could be found on TLC (thin layer chromatography). If the reaction was not complete after 16–20 hours, 50 mg more of DSC were added into the solution and the reaction checked again after 2 hours by TLC. (95% EtOAc and 5% MeOH were used as TLC solvent, iodine was used to visuzlize the spots.). To the solution was then added 2627 mg of DA-10 (quickly) and 1000 $\mu$L of triethyl amine. The reaction was stirred at room temperature for another 24 hours, and then 50 mL of $CH_2Cl_2$ added. The reaction solution was washed with water 3 times. The bottom organic layer was separated and dried with sodium sulfate. The white solid of CsA-DA-10 product was obtained after removal of all solvent by rotary evaperation and vacuum.

EXAMPLE 2

Synthesis of CsA-DA-10-HemiGlutarnate (HG)

In a 20 mL vial, about 550 mg of CsA-DA-10, 93.75 mg of glutaric anhydride and 10 mL $CH_2Cl_2$ were placed; 344 $\mu$L of triethyl amine was added and the reaction solution stirred at room temperature for about 2 hours. To the reaction solution was then added 40 mL of $CH_2Cl_2$, and washed with 1N HCl twice and water twice. The organic layer was dried with sodium sulfate, and solid CsA-DA-10-HG was obtained after removal of all solvent.

EXAMPLE 3

Conjugation of CsA-DA-10-HG With Bovine gamma globulin (IgG)

A: 4 mg/mL of Bovine gamma globulin Solution: 500 mg of IgG dissolved into 125 mL of 0.1M $Na_2CO_3$ (pH 9.5).

B: Activation of CsA-DA-10-HG with 2-Fluoro-1methylpyridinium p-toluenesulfonate (FMPT).

134.6 mg of CsA-DA-10-HG (0.0894 mmol) and 38.1 mg of PMPT (0.1345 mmole) were weighed. 4800 $\mu$L of dried $CH_3CN$ to dissolve the solids was added. 28.1 $\mu$L of TEA was then added. The reaction was stirred at room temperature for 2 hr.

C: Coupling of CsA-DA-10-HG to protein

The above activated CsA-DA-10-HG solution was added to the 4 mg/mL of Bovine gamma globulin solution with stirring, allowing each drop to disperse before the next one was added. After the addition was complete, the solution was allowed to stir gently for about 18 hours at room temperature. The solution was dialyzed (12,000 MW cut-off dialysis tube) in a cold room against 6 changes of PBS buffer solution. The dialyzed solution was diluted to 2 mg/mL of the protein concentration by adding fresh dialysis PBS buffer. 324 mg of brontopol was added to the container and agitated until it completely dissolved and was uniformly dispersed.

EXAMPLE 4

Coupling CsA-Bovine gamma globulin Conjugate to a Magnetic Particle 40 ml of above CsA-IgG conjugate was added into 40 ml of glutaraldhyde activated chromium dioxide solution. (The detailed procedure of preparation of activated chromium dioxide particle is disclosed in U.S. Pat. No. 4,661,408, the disclosure of which is incorporated herein by reference). The reaction was rotated at 4° C. for 24 hours. 32 ml of 30% BSA was added into the solution, the reaction rotated at room temperature for another 16–20 hours. 112 ml of 2 M glycine buffer was added into the above solution to quench the reaction for about 1 hour. The solution was washed with water three times and chrome diluent three times. The chromium dioxide particle was diluated to 40 ml with chrome diluent.

| Chrome diluent: | |
| --- | --- |
| Polymerized BSA (30%) | 15.1 g/L |
| Treholose | 28.7 g/L |
| Carbowax | 4.8 g/L |
| Proclin | 5 mL/L |
| Nemycin Sulfate | 0.06 g/L |

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

What is claimed is:

1. An enzyme-linked immunoassay for the measurement of cyclosporin A levels in whole blood samples comprising the steps of:

(a) lysing red blood cells in a sample of whole blood containing cyclosporin A;

(b) contacting the lysed whole blood sample with excess labeled anti-cyclosporin antibody, to form a labeled antibody-cyclosporin A complex;

(c) separating unbound antibody from the complex by contacting the mixture formed in step (b) with a solid phase comprising a cyclosporin derivative having the structure:

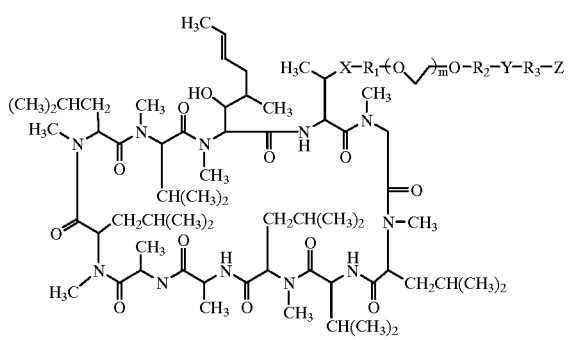

wherein X is selected from the group consisting of:

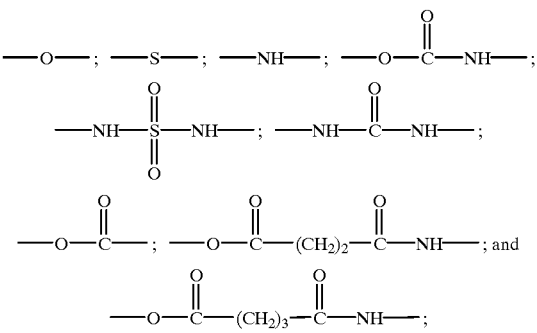

wherein Y is selected from the group consisting of:

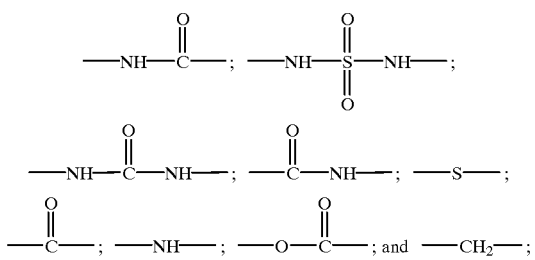

wherein Z is selected from the group consisting of:

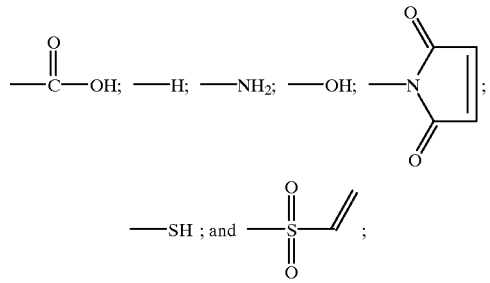

wherein $R_1$ and $R_2$ are each a $C_1$–$C_8$ alkyl group;
wherein $R_3$ is a bond or $C_1$–$C_8$ alkyl group; and
wherein m is 1–200,
immobilized on a solid support; and (d) determining the amount of the label in the complex as a measure of cyclosporin A.

2. The immunoasssy of claim 1, wherein the label is beta-D-galactosidase.

3. The immunoasssy of claim 2, wherein the amount the of beta-D-galactosidase label in the complex as a measure of cyclosporin A is determined by adding a beta-D-galactosidase substrate selected from the group consisting of chlorophenol red-beta-D-galactopyranoside and resorufin-beta-D-galactopyranoside.

4. The immunoassay of claim 1 wherein the solid phase is a stabilized chromium dioxide particle.

5. A composition of matter which comprises a conjugate of a carrier and a compound selected from the group consisting of:

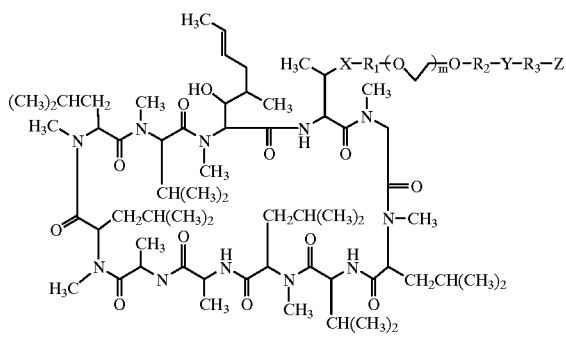
wherein X is selected from the group consisting of:
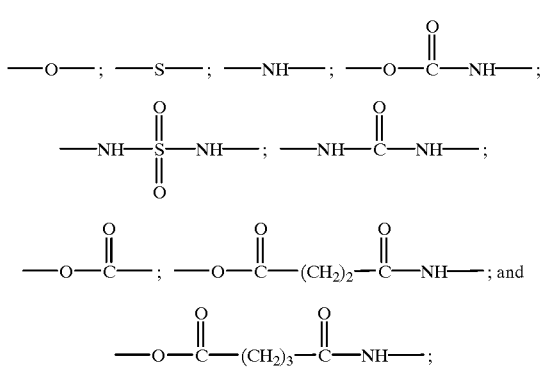
wherein Y is selected from from the group consisting of:
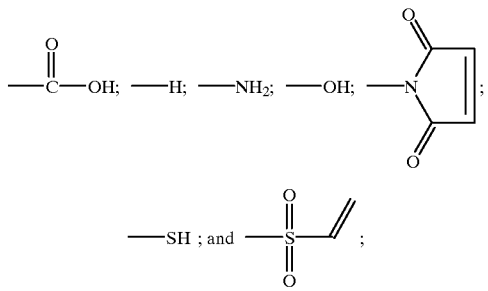
wherein Z is selected from the group consisting of:
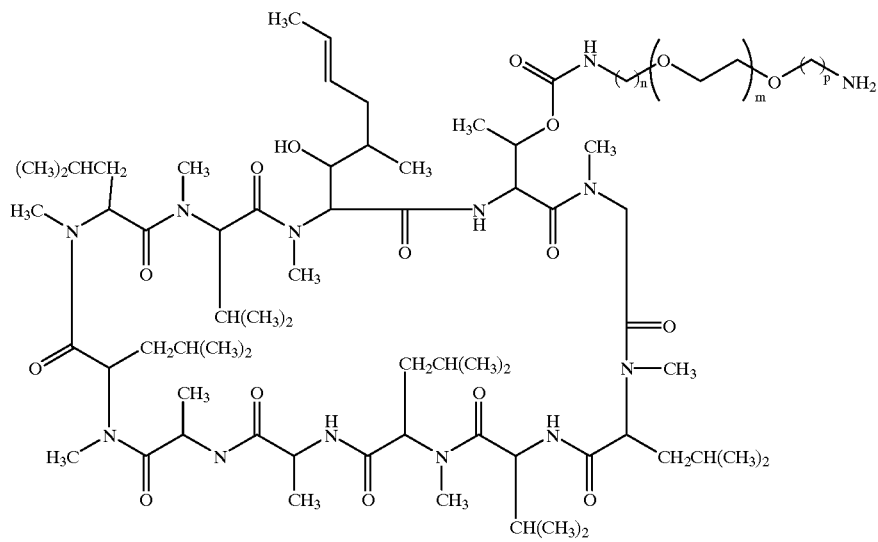
wherein $R_1$ and $R_2$ are each a $C_1$–$C_8$ alkyl group;
wherein $R_3$ is a bond or $C_1$–$C_8$ alkyl group; and
wherein m is 1–200,
wherein n is 2–3; m is 2–5 and p is 2–3, and

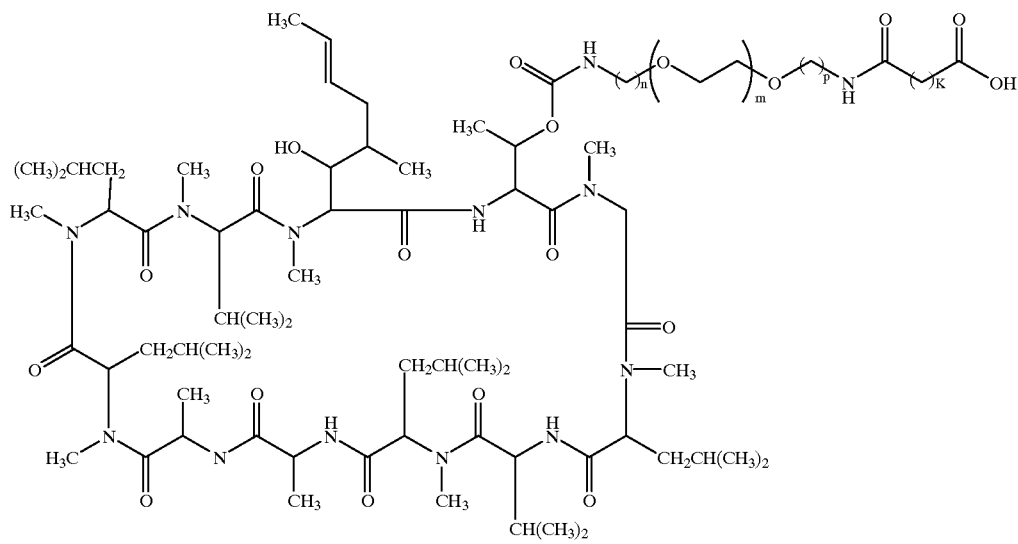

wherein n is 2–3; m is 2–5; p is 2–3 and k is 2–3.

6. The composition of matter of claim 5, wherein the carrier is immunogenic.

7. The composition of matter of claim 6, wherein the immunogenic carrier is a protein.

8. The composition of matter of claim 7, wherein the protein is selected from the group consisting of bovine serum albumin, keyhole limpet hemocyanin and ovalburnin.

9. The composition of matter of claim 5, wherein the carrier is a particle.

10. The composition of matter of claim 9, wherein the particle is a chromium dioxide particle.

11. Antibodies prepared in response to the composition of claim 6.

* * * * *